United States Patent [19]

Simmons et al.

[11] Patent Number: 5,405,602
[45] Date of Patent: Apr. 11, 1995

[54] NONAQUEOUS COLD STERILANT

[76] Inventors: Paul L. Simmons, 6250 Kipps Colony Ct. #203, Gulfport, Pinellas County, Fla. 33707; Ted Turner, 1810 Nebraska Ave. S.E., St. Petersburg, Fla. 33703

[21] Appl. No.: 901,592

[22] Filed: Jun. 19, 1992

Related U.S. Application Data

[63] Continuation-in-part of Ser. No. 642,709, Jan. 17, 1991, Pat. No. 5,145,663, which is a continuation of Ser. No. 304,312, Jan. 31, 1989, abandoned.

[51] Int. Cl.⁶ .......................... A61L 2/18; A61L 9/14; A61K 31/045; A61K 9/12
[52] U.S. Cl. ........................................ 424/47; 424/45; 424/76.8; 514/975; 422/28
[58] Field of Search ..................... 424/47, 76.8; 422/7, 422/28

[56] References Cited

U.S. PATENT DOCUMENTS

| | | | |
|---|---|---|---|
| 3,282,775 | 11/1966 | Stonehill | 422/36 |
| 3,821,413 | 6/1974 | Hellyer, Jr. | 514/738 |
| 3,968,250 | 7/1976 | Boucher | 514/705 |
| 4,511,486 | 4/1985 | Shah | 424/45 |

*Primary Examiner*—Edward J. Webman
*Attorney, Agent, or Firm*—A. W. Fisher, III

[57] ABSTRACT

A hypocompatible biodegradable nonaqueous cold chemical sterilant capable of killing a challenge of a wide range of target organisms including bacterial spores within ten minutes comprising a composition of interactive constituents including a monohydric alcohol, a polyhydric alcohol, a saturated dialdehyde and a cationic surface active agent in proportion by weight to reduce the surface tension of the bacterial spore wall, penetrate the bacterial spore wall and kill the nuclei of the bacterial spores and other target organisms without the need of removing residue.

6 Claims, No Drawings

NONAQUEOUS COLD STERILANT

This application is a continuation-in-part application of application Ser. No. 642,709, filed Jan. 17, 1991, now U.S. Pat. No. 5,145,663, that is a continuation application Ser. No. 304,312, filed Jan. 31, 1989, now abandoned.

BACKGROUND OF THE INVENTION

1. Field of the Invention

A hypocompatible biodegradable non-aqueous cold sterilant effective against a wide range of pathogenic organisms including bacterial spores.

2. Description of the Prior Art

Sterilants are used in many areas, such as in the sterilization of laboratory, surgical, dental and other equipment. It is customary in hospital practice to sterilize instruments overnight, using chemical sterilizing agents or other sterilizing methods.

The most common methods of sterilization involve either the use of pressurized steam, dry heat or ethylene oxide. However, some of these methods are cumbersome, tedious and time-consuming, often damage the sterilized material and require expensive equipment and skilled technicians.

Moreover, steam sterilization is impracticable for many plastic devices and delicate instruments which are sensitive to elevated temperatures.

Many chemical sterilization methods have been developed as substitutes for steam sterilization. Unfortunately most have shortcomings. Phenols and formaldehyde compositions have considerable sporicidal activity but have objectionable odors and extreme toxicity. Ethanol, isopropyl alcohol and the quaternary ammonium compounds have been used, and though less odorous and toxic, lack the activity of the phenols and formaldehyde compositions.

Compositions comprising saturated dialdehydes with alkalinating agents have also been used. Though such compounds are satisfactory as chemical sterilization agents their sporicidal activity is limited to certain pH ranges, require up to ten (10) hours to work, and have certain limits on stability.

U.S. Pat. No. 3,282,775 shows a sporicidal composition including saturated dialdehydes containing from 2 to 6 carbon atoms and a cationic surface active agent. More specifically, these compounds include malonaldehyde, succinaldehyde, oxaldehyde (glyoxal), adipaldehyde and preferably, glutaraldehyde. The quantity of saturated dialdehyde used may vary from about 0.1 percent to about 2 percent depending upon which particular dialdehyde is selected. Moreover, one may safely depart from this concentration without seriously detracting from its effectiveness. For example, if desired, the final concentration of dialdehyde may be increased up to as much as 10 percent or decreased as low as 0.05 percent. However, amounts in excess of 2 percent are unnecessary, extremely toxic and wasteful. In actual practice a range of from 0.1 percent to about 2 percent is preferred. The compounds may be diluted either with water or lower alkanols such as methanol, ethanol, isopropanol and the like, or with combinations to form aqueous-alcohol solutions. The pH of the final solution may be either on the acid side or the alkaline side and may be varied over a wide range of from about 4.0 to about 9.0 though it is preferred to have the pH in the range of from about 5.0 to 8.0.

U.S. Pat. No. 4,040,977 describes a preservative and disinfecting composition for aqueous emulsions, suspensions and solutions which are obtained by reaction in water of a haloacetamide or thiocyanoacetamide or mixture thereof; an alcohol or mixture of alcohols; and formaldehyde.

U.S. Pat. No. 3,697,222 describes a sterilization process achieved by contacting a contaminated object with an aqueous acid glutaraldehyde solution at temperatures above about 45 degrees C. The sterilizing action may be enhanced by ultrasonic energy. Sterilization also may be achieved using ultrasonic energy and aqueous alkaline glutaraldehyde solution.

U.S. Pat. No. 4,093,744 teaches a means for killing spores on instruments and the like utilizing the combination of glutaraldehyde and a detergent selected from the group consisting of nonionic, anionic and ampholytic surface active agents. The sporicidal kill activity of glutaraldehyde is enhanced by the detergents.

U.S. Pat. No. 4,048,336 relates to a means for killing spores on instruments and the like utilizing the combination of 18 glutaraldehyde and a monoaldehyde, such as, for example, formaldehyde. The sporicidal kill activity of the composition is more rapid than previously possible and more effective than the use of either glutaraldehyde or monoaldehyde alone. Unfortunately, this composition is far more toxic than without glutaraldehyde.

U.S. Pat. No. 4,208,404 shows an aqueous solution of glutaraldehyde of acid pH value with dissolved quantities of certain highly ionized salts to kill dormant spores at room temperature.

U.S. Pat. No. 4,294,797 describes a composition to sterilize medical instruments comprising an alcohol-aldehyde active substance combination in a proportion of 5 to 15 percent by weight. The preferred alcohol is isopropanol and the preferred aldehyde is formaldehyde or a succinic acid dialdehyde complex and the preferred ratio of alcohol to aldehyde is 1:1.

U.S. Pat. No. 2,889,243 shows a chemical composition having antiviral activity comprising hydroxpyruvaldehyde ether.

U.S. Pat. No. 4,173,653 teaches an Oxydiacetaldehyde is used as an active antimicrobial agent in an aqueous solution for disinfecting or sterilizing. The activity against bacteria or spores can be improved by adding alkalinating agents or alcohols such as isopropanol, or by raising pH or by raising the temperature.

U.S. Pat. No. 4,923,899 describes an aqueous composition for killing bacteria, spores, fungi and viruses on nonabsorbent surfaces comprising at least one quaternary ammonium salt, at least one aliphatic dialdehyde having from two to six carbon atoms, and at least one aliphatic hydroxyl compound having from one to eight atoms. Optionally, a chelating agent and an inorganic nitrite salt may be employed. This sterilant kills bacteria, spores, fungi and viruses over a pH range from about pH 4 to about pH 9.

U.S. Pat. No. 3,968,250 describes a method for disinfecting or sterilizing medical, surgical, dental instruments or other objects in liquid phase with improved sporicidal compositions by combining nonionic and anionic surfactants with aqueous or alcoholic glutaraldehyde solutions. The method can be used also with ultrasonic irradiation over a wide frequency range of from 10 to 850 kHz.

U.S. Pat. No. 3,968,248 and U.S. Pat. No. 3,912,450 teach similar methods.

U.S. Pat. No. 4,103,001 shows a room temperature aqueous sterilizing composition comprising from 0.75 percent by weight of glutaraldehyde and from 4-15 percent by weight of phenol and a metal phenate, preferably sodium phenate. Optionally present are 1-5 percent by weight of sodium tetraborate, 2-10 percent by weight of a humectant such as glycerol, di-ethylene glycol or propylene glycol and a surfactant. A preferred pH range is pH 7.0-7.4.

U.S. Pat. No. 4,004,024 describes a method for controlling bacteria, fungi and spores which comprises applying thereto a bacterially, fungicidally and sporicidally effective amount of a furan selected from 2-($R_1$O)-5-($R_{20}$O)-2,5-dihydrofuran and 2-($R_1$O)-5-($R_2$O)-tetrahydrofuran or mixtures thereof; a process for preparing a 2,5-bis(-$R_1$O)-2.5-tetrahydrofuran and 2.5-bis((-$R_1$O)-tetrahydrofuran and 2.5-bis(benzyloxy)-tetrahydrofuran.

U.S. Pat. No. 4,436,754 describes a disinfecting and sterilizing composition comprising an aqueous solution containing a 2 to 6 carbon atom dialdehyde and may also contain formaldehyde and a diol or monosubstituted diol of the formula RO($CH_2YCH_2O)_n CH_2CH_2OH$; where R is H or $CH_3$ and n is an integer from 1 to about 22 with a wide range of pH from pH 2 to pH 9.

U.S. Pat. No. 4,937,072 a sporicide having a defined period of sporicidal activity comprising three components including a peroxide or peroxide generating material, a peroxidase and a salt of iodine which serves as a donor molecule, storing the three components in a non-reacting state to maintain the sporocide in an inactive state and admixing the three components in an aqueous based carrier to cause a catalyzed reaction by said peroxidase for generating free radicals and/or by-products from the iodide salt (donor molecule) and contacting the surface or object to be sterilized with the activated mixture. The concentration level of the three components can be selected such that an active sporocidal state is maintained for any desired period of time.

U.S. Pat. No. 4,122,192 describes a solid composition for producing a disinfectant or sterilant comprising a disinfecting or sterilizing amount of saturated dialdehyde having from 2 to 6 carbon atoms absorbed on an inorganic or organic particulate carrier material and, in some cases, an alkalinating agent.

U.S. Pat. No. 3,983,252 describes a disinfectant composition comprising a dialdehyde and an alkali metal salt of a hydrocarbon carboxylic acid in aqueous solution and, optionally, an alcohol and/or a diol and/or a triol, and are as potent as, but substantially more stable than, known dialdehyde containing disinfectant compositions.

U.S. Pat. No. 3,653,499 describes a germicidal, sporicidal and detergent composition which prevents coagulated blood from adhering to instruments during sterilization and used to decontaminate surgical items, such as needles and sponges comprising paraformaldehyde having an average molecular weight of about 360 free from polymer chains over a molecular weight of 3,000, alkali metal tripolyphosphate and a water soluble buffer, such as sodium carbonate, to give a final aqueous solution having a pH between about 10 and 11. If the materials are substantially anhydrous, the constituents can be mixed together in a powder and stored in a container hermetically sealed against the entrance of moisture. If the constituents or any of them are not substantially anhydrous, the composition must be in a two-part package separately sealed in waterproof pouches, one containing the paraformaldehyde and the other the polyphosphate and buffer.

U.S. Pat. No. 4,978,530 describes a process for sanitizing, disinfecting and killing spores involving providing a tangible object made from polymeric material impregnated with an aqueous glutaraldehyde solution packaged in an air-tight enclosure, removing the impregnated tangible object from the enclosure and applying the impregnated tangible object to the surface to be sterilized and/or sanitized and disinfected so as to expose spores, bacteria, virus and other microorganisms present on the surface to the action of the glutaraldehyde solution. A sanitary attachment for a receiver or mouthpiece of a telephone made from plastic material incorporating a glutaraldehyde solution. A fabric made from cellulosic or plastic material having sporicidal and/or sanitizing and disinfectant activity as a result of being impregnated with a glutaraldehyde solution. A method for sanitizing and disinfecting and/or rendering fabric sporicidal involves impregnating a fabric with an aqueous glutaraldehyde solution prior to packaging the fabric in an air-impervious container until ready for use.

Various spray germicides for sanitizing such surfaces is typified by U.S. Pat. No. 3,445,564. U.S. Pat. No. 3,445,564 is directed to a method, compositions and articles for sanitizing public or communal facilities prior to individual use. The method consists of applying a thin layer of a rapidly drying liquid germicidal composition to a surface such as a toilet seat. The rapidly drying germicidal compositions consist essentially of a lower aliphatic alcohol and at least about 5 percent of a volatizing agent such as acetone. Isopropyl alcohol has excellent germicidal activity and is sufficiently volatile to give a satisfactory drying rate when blended with suitable proportions of a volatizing agent. Inasmuch as the lower aliphatic alcohols are not sufficiently volatile to afford usefully short drying times for practical purposes in the method and articles of the Kirschner invention it was necessary to include a volatizing agent in the germicidal composition. The proportion of volatizing agent to lower aliphatic alcohol in the rapidly drying germicidal compositions employed in the invention may vary widely depending upon a number of factors, which include among others, the volatility of the alcohol employed, the volatility of the volatilizing agent, the desired drying rate of the germicidal composition, the amount of germicidal agent applied to the surface to be treated and the method of application of the germicide, not to mention the prevailing conditions of temperature and relative humidity under which the product is to be employed.

Although the isopropyl alcohol-acetone composition of U.S. Pat. No. 3,445,564 has germicidal activity against bacteria, fungi and other lower organisms, additional antibacterial, antifungal or other active ingredients may be incorporated to enhance the overall germicidal effectiveness. Suitable germicidal additives include the well known antibacterial quaternary ammonium compound. In essence, U.S. Pat. No. 3,445,564 teaches the use of isopropyl alcohol to kill a limited number of germs on a dry toilet seat with the addition of acetone to volatize an already highly volatile chemical to rapidly dry the toilet seat for use within 30 seconds.

The use of a dye in a bactericidal solution as disclosed in U.S. Pat. No. 2,449,274 is employed to provide a visual indication of the effectiveness of such sprays.

U.S. Pat. No. 4,678,658 shows an aerosol spray for use in disinfecting a surface for personal use such as a public restroom facility or telephone. The composition and delivery of the compositions provides for the placement of a spray of disinfectant which includes a dye that disappears as the spray effects the germicidal activity of the disinfectant. The composition is also rapidly drying, so that the dye disappears as well as the disinfecting composition leaving the surface dry. However, the spray is corrosive and environmentally unsafe.

U.S. Pat. No. 3,821,413 discloses a formulation of materials which permits an effective, uniform rate of evaporation of glycols from an air circulator device to reduce airborne bacteria in the surrounding atmosphere. It was observed that the relative amounts and identities of the components of the invention are critical to the attainment of the desired continuous evaporation of glycols over a prolonged period of time.

The composition of U.S. Pat. No. 3,821,413 is a single phase liquid composition especially adapted for volatilization at a substantially uniform rate from the air circulator device. Generally speaking, the composition includes three essential components (1) a glycol, (2) an organic polar coupling compound for maintaining the homogeneity prevents the glycol from separating from the mixture during evaporation of the mixture into the atmosphere and (3) an organic, relatively non-polar compound for forming hydrophobic micelles with the glycol molecules in the resulting mixture for reducing the affinity of the glycol to atmospheric moisture and thereby increasing the rate at which the glycol may be evaporated into the atmosphere.

The composition contains the glycol germicide. If desired, other suitable germicides or antiseptic agents can be added provided, however, that the glycol concentration of the composition does not fall below 5 percent by weight of the total mixture. Such germicides include quaternary ammonium compounds, phenols, bisphenols, salicylanilides, carbanilides, formaldehyde and chloride.

The required glycol evaporation rate for attaining the desired air sanitizing performance depends on the satisfactory stability and uniform nature of the liquid composition during evaporation from the mixture. Accordingly, the compositions of the invention include from about 2 percent to about 40 percent by weight of an organic polar coupling compound for maintaining the homogeneity of the mixture to prevent the glycol from separating from the mixture during the evaporation process.

The affinity of glycols to attract atmospheric moisture significantly reduces their volatility and impairs their evaporation rate. Accordingly, the compositions of the invention include from about 5 percent to about 80 percent by weight of an organic, relatively non-polar compound for forming hydrophobic micelles surrounding the glycol molecules in the mixture for reducing the affinity of the glycol to atmospheric moisture and thereby increase the rate of evaporation of the glycol. Without this micelle formation, it was found that the glycol or mixture of glycols in the mixture cannot evaporate appreciably in an air circulator device containing a wick immersed in the liquid composition.

U.S. Pat. No. 3,806,593 is directed to an acne treatment medication applied to the skin for preventing the formation of acne or decreasing already established ache. An important factor for the occurrence of ache is the presence of bacteria in the sebaceous glands in the skin. It is known that the bacteria in the sebaceous glands form esterases which hydrolyze the sebum fats to alcohols and free fatty acids.

The medicinal ache-preventing or ache-diminishing composition of U.S. Pat. No. 3,806,593 is based on the bacterial esterase activity in the sebaceous glands which together with the water already present in the skin can hydrolyze an ester having a good penetration capacity into the sebaceous glands to form one and preferably two antibacterially active components, viz. an acid and an alcohol, which are harmless to the skin. The active compound in the composition is one or more esters chosen from the group consisting of ethyl lactate, isopropyl lactate and/or glycerol mono or dilactate. The esters hydrolyze in the sebaceous glands due to the esterases present in the glands to form the corresponding acids and alcohols. Lactic acid and the lower alcohols and also glycerol to a certain extent exert a good antibacterial activity when formed in situ in the sebaceous glands. The esters are lipophilic and can thus penetrate into the said glands. Even if a beneficial action can be achieved by application of the ester or esters per se, it has been found to be suitable to apply the ester in the form of a solution in ethyl alcohol or isopropyl alcohol. The alcohol prevents hydrolysis of the ester already in the composition, the alcohol moves the hydrolysis equilibrium towards ester formation. The alcohol can also facilitate the penetration of the ester into the skin.

As is well-known alcohol in high concentrations may cause a drying-out of the skin. To counteract this effect, the composition may include a moisture-retaining agent such as a lower, suitably water-free polyol, viz. propylene glycol or glycerol. The content of propylene glycol or glycerol in the composition according to the invention may be up to 25 percent, suitably not more than 10 percent by weight and preferably 1–5 percent. High levels of polyol tend to make the composition smeary upon application on the skin and should thus be avoided.

The preferred composition according to the invention consists of about 15 percent by weight of ethyl lactate, about 2 percent by weight of propylene glycol, the remainder being ethyl alcohol.

In summary, U.S. Pat. No. 3,806,593 relates to acne medication comprising esters that hydrolize in the sebaceous glands in combination with an alcohol to prevent hydrolysis of the esters as well as to facilitate the penetration of the ester into the skin, and propylene glycol or glycerol to prevent drying of the skin. The preferred ratio of the constituents is 15 percent to 83 percent to 2 percent respectively.

U.S. Pat. No. 4,664,909 discloses a stable, fast drying pituitous powder deodorant suspension in an alcohol media containing a minimal amount of water and a critical amount of the essential hydroxyethyl cellulose as the suspending agent.

The fast drying pituitous suspension of particulate material in an aqueous alcohol media contains hydroxyethyl cellulose at levels above its normal solubility limit by the polyhydric alcohol.

More specifically, U.S. Pat. No. 4,664,909 relates to stable pituitous suspensions of particulate material, preferably about 1–20 percent, uniformly suspended in alcohol/aqueous media containing a high alcohol content and a lower water content. The alcohol media may be a lower monohydric alcohol selected from the group consisting of methanol, ethanol, isopropanol and mixtures thereof. The use of polyhydric alcohols such as propylene glycol, butylene glycol and polyols thereof, and glycerin decreases the critical water level required in the hydroxyethyl cellulose-containing alcohol media.

It has been unexpectedly found that powders can be suspended in alcoholic/aqueous media containing a high alcohol content and a lower water content by using the water soluble polymer hydroxyethyl cellulose at critical levels above its ethanol solubility range which may be broadened by specified polyhydric alcohols. This polymer is unique in its property to form stable suspensions.

Specifically, polyhydric alcohols can be partially substituted for the monohydric alcohol, not to exceed the monohydric alcohol content. The monohydric alcohol content, such as ethanol, must exceed the upper solubility level for the water soluble polymer hydroxyethyl cellulose in ethanol or other lower alkanol. The reported upper solubility level of this water soluble polymer in ethanol is 70 percent. Below this level and within normal soluble use ranges, a uniformly viscous liquid is obtained which pours evenly. Although, it appears aesthetically desirable, it will not support suspended powder and segregation occurs. However, at ethanol concentrations above its solubility range, the polymer becomes less soluble and forms the desired pititious type liquid. If ethanol is further increased resulting in very low water levels the polymer will precipitate out and its suspending properties are again lost. Accordingly, a 70:30 ratio of ethanol-water is optimum. However, it was found that this problem can be eliminated by the sufficient addition of a polyhydric alcohol such as glycerin, propylene glycol, butylene glycol and polyglycols thereto.

Accordingly, it has been found that the monohydric alcohol constitutes about 55-85 percent; and the water content may be as low as 5 percent if at least 10 percent polyhydric alcohol is also present in the suspension. The combined water and polyhydric alcohol content is at least 15 percent and may be up to about 25 percent. Thus, it is apparent that the proportions of monohydric alcohol, water and polyhydric alcohol are interdependent.

In summary, U.S. Pat. No. 4,664,909 teaches a fast-drying deodorant comprising a critical amount of hydroxyethyl cellose as the deodorant to encapsulate or isolate bacteria to prevent growth of the bacteria, suspended in a solution of monohydric alcohol to provide the fast drying characteristics and polyhydric alcohol to improve the overall solubility of the solution to allow the use of increased levels of monohydric alcohol. The relative proportions of the monohydric alcohol, water and polyhydric alcohol are driven or determined by the desired solubility and therefore are interdependent.

U.S. Pat. No. 3,966,902 disclosed various polymer complex carriers such as propylene glycol for use with an active ingredient such as a disinfectant or fragrance.

U.S. Pat. No. 4,690,779 refers to the use of propylene glycol in combination with alcohol and fragrances. This composition is both toxic and non-biodegradable.

U.S. Pat. No. 4,209,500 teaches a composition suitable for use in aerosol sprays including an anhydrous alcohol and fragrance or perfume. This composition is corrosive, non-biodegradable and non-evaporative.

U.S. Pat. No. 4,689,168 describes a hard surface cleaning composition suitable for glass, chrome, plastic, enamel and other hard surfaces. The composition is applied to the hard surface as an emulsion of an aqueous phase and an oil phase. The bubbling action is caused by the evaporation of volatile constituents from the film or layer of applied compositions, as well as the desire for the aqueous and oil phase components to reform. The bubbling action, characterized by small bubbles of volatile components erupting from the surface of the composition film aids in lifting soil from the hard surface. As an apparent consequence, the rate of cleaning is accelerated. The composition comprises a polar organic solvent or mixture of solvents, a nonvolatile surfactant, a volatile surfactant such asn an acetylenic alcohol or diol, a volatile organosiloxane oligomer and water.

U.S. Pat. No. 4,983,317 teaches a liquid composition for cleaning a wide variety of hard surfaces, particularly metallic, plastic, tile, porcelain, glass and mirrored surfaces comprising a polyacrylic acid or a polyacrylate resin builder in combination with a hydrotrope which is an alkali metal salt of a $C_{21}$ dicarboxylic acid. The organic solvent may be selected from the group consisting of alkylene and polyalkylene glycols of from 2 to 6 carbon atoms and lower alkyl ethers of alkylene and polyalkylene glycols of from 3 to 8 carbon atoms, the alkyl ether having from 1 to 4 carbon atoms. A lower aliphatic alcohol of from 2 to 4 carbon atoms may also be included in the composition to adjust evaporation rate of the composition.

U.S. Pat. No. 5,064,635 describes a mixture of one or more surfactants (detergents) with the pH sensitive dye. The surfactant can be diluted with water to give the desired cleaning strength. The surfactant can be an anionic, nonionic, amphoteric or mixtures of the three types. Typical anionic surfactants used are petroleum sulfonates, such as sodium dodecylbenzene sulfonate, alcohol sulfates such as sodium lauryl sulfate and ethoxylated higher fatty alcohol sulfates such as sodium lauryl ether sulfate. Typical nonionic surfactants are primary alcohol ethoxylates, secondary alcohol ethoxylates, alkyl phenol ethoxylates and alkanolamides. The amphoteric surfactants include a number of types of carboxylates derived from fatty imidazolines such as sodium dicarboxyethylcoco phosphoethyl imidazoline or fatty proprionates such as cocoamphoproprionate or cocoamphodipropionate. The composition of a basic cleaner includes the surfactant or mixture of surfactants at about 0.1 percent to about 20.0 percentage by weight. This range of surfactant is for usage in a nondiluted product for household use. Thymolphthalein in the range of about 0.01 percent to about 1 percent by weight will give a broad range of blue color when varying intensity using an alkali system to adjust the pH of the composition.

U.S. Pat. No. 4,965,063 and U.S. Pat. No. 5,057,303 teach compositions similar to U.S. Pat. No. 5,064,635.

U.S. Pat. No. 4,329,334 shows a homogeneous liquid anionic-amphoteric based antimicrobial conditioning shampoo which includes about 0.5 to 2.5 percent of the antimicrobial agent, 1-imidazolyl-1-(4-chlorophenoxy)-3, 3-dimethylbutan-2, one, solubilized in an aqueous solution of critical amounts of a mixture of the following specific ingredients: about 10-40 percent by weight of an anionic sulfate or sulfonate surface active agent; about 0.1-7.5 percent by weight of an amphoteric surfactant selected from the group consisting of cocobetaine, cocosulfobetaine, cocoamidopropylbetaine, cocoamidopropylsulfobetaine or combinations thereof; a nonionic surface active agent selected from the group consisting of a tertiary amine oxide, a polyoxyethylene hexitan mono-higher fatty acid ester and mixtures thereof; and about 0.5-2 percent by weight of a lower aliphatic monohydric or polyhydric alcohol or mixtures thereof in certain critical amounts to avoid precipitation of the antimicrobial agent.

U.S. Pat. No. 3,654,165 teaches a cleaner-sanitizer for use on telephone instruments including a fast-acting, penetrative, quick-drying bacteriocidal detergent solution which leaves a safe, active residue of selected proportions of sodium lauryl sulfate, dimethyl sulfone, isopropanol and iodine in solution.

U.S. Pat. No. 4,793,988 describes a composition for disinfecting a surface, such as a public restroom facility or telephone. The composition and delivery of the composition provides for the placement of a thin layer of disinfectant including a dye. The dye disappears as the thin layer effects the germicidal activity of the disinfectant. A sample of the germicidal composition was prepared with 400 mg of sodium dodecyl sulfate (SDS), 400 mg of octyl phenoxy polyethoxyethanol marketed as Triton X-100 and 100 mg of blue dye thymophthalein. This composition was tested for germicide effectiveness against Herpes simplex virus type 2, Neisseria gonorrhoeae, Staphylococcus aureus, Escherichia coli 011K58, Shingela sonnei, Salmonella typhimurium and Candida albicans.

U.S. Pat. No. 4,975,217 describes germicidal compositions for direct application to human skin including an organic acid, e.g., malic acid, and an anionic surfactant, e.g., a sodium alpha-olefin sulfonate, as active ingredients, and can optionally include an alcohol, e.g., specially denatured ethyl alcohol, as an additional active ingredient. When formulated as soaps and lotions, the compositions have been found to produce more than a 2.0 log reduction in bacteria applied to skin. Organic acids and anionic surfactants, e.g., malic acid and a sodium alpha-olefin sulfonate surfactant, are used as active ingredients in germicidal products which are applied directly to the skin, such as hand-washing soaps, skin-care lotions, soapy-lotions, or wipes containing these materials. Optionally, the products can include an alcohol, such as, specially denatured ethyl alcohol, ethyl alcohol and isopropyl alcohol as an additional active ingredient. These formulations, in addition to killing viruses, also effectively kill bacteria and yeasts. In particular, the formulations have been found to kill a variety of microorganisms in both in vitro experiments performed in test tubes and, even more importantly, in in vivo experiments performed on human hands. Moreover, notwithstanding their germicidal activity, the formulations have been found to be non-irritating to human skin.

U.S. Pat. No. 4,046,706 shows a composition for cleaning contact lenses comprising a poly(oxyethylene)-poly(oxypropylene) block copolymer having a molecular weight between 1900 and 15,500, a water solubility in excess of about 10 gms per 100 nl, a cloud point in 1 percent aqueous solutions above about 30 degrees C., and a foam height in excess of 30 mm; a microbial growth inhibitor; ethyl or isopropyl alcohol; an amphoteric surfactant and water.

U.S. Pat. No. 3,578,499 teaches a powder composition containing a gelling agent, a neutral diluent, a wetting agent and a dye or coloring additive. The powder gelling composition when added to water forms a gel. Acid or alkaline materials are added for cleaning, biocidal agents for sanitizing or other materials to produce a desired effect. The significant advantage of this method is the increased residence time and hence contact time between agents in the gel and the surface to be acted on.

A third component included in the gelling composition is a wetting agent exemplified by a linear alkyl benzene sulfonate type material wherein the alkyl group may include from about 12 to 14 carbon atoms. The wetting agent should be desirably characterized as a anionic agent although it is recognized that nonionic surfactants may also be employed. One wetting agent found useful herein is the commercially available sulfonate of dodecylbenzene.

U.S. Pat. No. 2,333,124 describes a method for sterilizing air laden with bacteria or other pathogenic organisms comprising contacting the air with a mixture of glycols in vapor form in proportions to provide about 1 gram of such glycols in vapor form to not more than about 5 to 7 million cubic centimeters of air.

U.S. Pat. No. 2,857,315 shows a stable anti-perspirant stick having a base comprising a sodium stearate-propylene glycol soap gel having an active anti-perspirant agent sodium zirconium lactate. The sodium stearate-propylene glycol soap gel may contain alcohol in an amount not substantially greater than the propylene glycol by weight.

Additional examples of the prior art are found in U.S. Pat. No. 580,213; U.S. Pat. No. 3,282,776; U.S. Pat. No. 4,201,764; U.S. Pat. No. 4,282,179; U.S. Pat. No. 4,265,899; U.S. Pat. No. 4,283,421; U.S. Pat. No. 4,364,515; U.S. Pat. No. 4,550,105, U.S. Pat. No. 4,105,431; U.S. Pat. No. 4,243,403; U.S. Pat. No. 4,278,206; U.S. Pat. No. 4,322,475; U.S. Pat. No. 4,436,732; U.S. Pat. No. 4,464,293; U.S. Pat. No. 4,597,887, U.S. Pat. No. 4,252,694; U.S. Pat. No. 4,279,762; U.S. Pat. No. 4,325,201; U.S. Pat. No. 4,540,505; U.S. Pat. No. 4,675,397 and U.S. Pat. No. 4,915,934.

Examination of the prior art reveals most existing compositions available are either toxic or non-biodegradable or both. Toxic chemicals that are not biodegradable contaminate our environment, the soil and the water supply.

In recognition of the dangers of existing disinfectants, health facilities are required to notify employees that toxic chemicals are in use and advise them of the possible hazards that result or could result as a consequence of misuse or a spills. Such notices must also be given to the community at large.

Other laws and regulations require users to document the use of toxic chemicals and require that the excess, the waste, or the residue be collected and properly stored. These materials must be collected by licensed and approved toxic waste companies, taken to an authorized disposal site and legally destroyed. The cost of disposing of such toxic material is often more expensive than the initial purchase price.

Sterilants today should be non-toxic or low in toxicity and biodegradable and capable of killing bacterial spores quickly and effectively. Further, such disinfectants and sterilants should be chemically compatible with the numerous aparatus and instruments found in modern healthcare facilities.

As described more fully hereinafter the instant invention is directed to an environmentally safe composition capable of killing anaerobic and aerobic bacteria, viruses including the HIV virus, mildew, mold, fungus and bacterial spores. The principal complementary sporicidal ingredients of the invention are selected from a group of monohydric alcohols, a group of polyhydric alcohols, a group of saturated dialdehydes and a group of cationic surface active agents.

In the past such alcohols have had limited use outside the laboratory due to various undesirable characteristics of alcohol. For example, it has been universally accepted that alcohol has very limited application as a widely used disinfectant because alcohol is unable to penetrate protein rich material, evaporates quickly, has limited stability and shelf life, has a pungent odor and tends to form a glaze on hard surfaces possibly hiding or covering visible contamination.

The instant invention has evolved from an extensive development program involving the unexpected formulation of certain chemicals to reduce or inhibit those undesirable features of alcohol and to make alcohol safe and effective for use outside the laboratory.

SUMMARY OF THE INVENTION

The present invention relates to a hypocompatible biodegradable nonaqueous cold chemical sterilant for use in manual bucket systems as well as automated sterilizer systems to kill a wide range of pathogenic organisms including bacterial spores.

The cold chemical sterilant comprises a composition including a monohydric alcohol, a polyhydric alcohol, a saturated dialdehyde and a cationic surface active agent.

The monohydric alcohol is selected from the group consisting of isopropyl, methyl, ethyl, n-propyl, n-butyl, tert-butyl alcohol and allyl alcohol and mixtures thereof. The polyhydric alcohol is selected from the group consisting of propylene glycol; 1,3 propanediol; 1,2 butanediol, polyethylene glycol with molecular weight of less than 800; glycerol and 1,4 butanediol and mixtures thereof.

The saturated dialdehyde is selected from the group consisting of malonaldehyde, succinaldehyde, oxaldehyde (glyoxal), adipaldehyde and glutaraldehyde. The cationic surface active agent is selected from the group consisting of cetylpyridinium chloride, methylbenzethonium chloride, dodecylamine, hexadecylamine, hexadecylamine hydrochloride, dodecyl aniline, oleyl methylamine ethylene diethylamine methyl sulfate, oleyl benzylamino ethylene diethylamine hydrochloride, sulfate of lauryl pyridinium, octadecyl methylene pyridinium acetate, methyl sulfate of dimethyloctadecyl sulfonium, betaine of diethyl aminoacetic acid, cetylpyridinium bromide, dodecyltrimethylammonium bromide, hexadecyltrimethylammonium bromide, tetradecyltrimethylammonium bromide, benzalkonium chloride, benzethonium chloride, benzyldimethyldodecylammonium bromide, benzyldimethyl- hexadecylammonium chloride, benzyldimethyltetradecylammonium chloride, benzyltrimethylammonium methoxide, cetyldimethylethylammonium bromide, decamethonium bromide, dimethyldioctadecylammonium bromide, methylbenzethonium chloride, methyl mixed trialkylammonium chloride, methyltrioctylammonium chloride, 4-picoline dodecyl sulfate, n,n,n'poloxyethylene (10)-n-tallow-1,3-diamino propane and octadecyl chloromethyl ether.

The relative proportions by weight of each of the four constituents compliment each other to reduce the surface tension of the bacterial spore wall, penetrate the bacterial spore wall and kill the nuclei of the bacterial spores and other target organisms without the need of removing residue.

The hypocompatible biodegradable nonaqueous cold chemical sterilant in liquid form may be used in manual bucket systems or automatic sterilizer systems. Alternate systems may include a towelette or an absorbent wipe containing the product in an airtight enveloping material such as sealed foil or other wrapping material could be used for a single application.

The invention accordingly comprises the features of construction, combination of elements, and arrangement of parts which will be exemplified in the construction hereinafter set forth, and the scope of the invention will be indicated in the claims.

DETAILED DESCRIPTION OF THE PREFERRED EMBODIMENT

Various sterilizing compositions and delivery devices have been developed to kill various pathogenic organisms including bacterial spores. The wide range of application or use is limited by the chemical and biological effect of such compositions on the various surfaces and delivery means exposed to such compositions.

The present invention relates to a hypocompatible organic or nonaqueous cold chemical sterilant for application on medical instruments, and other devices which is effective against a wide range of target organisms including bacterial spores.

The cold chemical sterilant comprises a hypocompatible biodegradable nonaqueous or organic composition including a monohydric alcohol, polyhydric alcohol, saturated dialdehyde and a cationic surface active agent combined in relative proportions by weight to sterilize medical and dental instruments and other devices such as scopes and dental handpieces. The application of the cold chemical sterilant is capable of killing a challenge of the pathogenic or target organisms discussed herein within ten minutes and without leaving an unacceptable residue.

The monohydric alcohol is selected from the group consisting of isopropyl, methyl, ethyl, n-propyl, n-butyl, tert-butyl and allyl and mixtures thereof. The preferred monohydric alcohol is isopropyl.

The polyhydric alcohol is selected from the group consisting of propylene glycol; 1,3 propanediol; 1,2 butanediol, polyethylene glycol, glycerol and 1,4 butanediol and mixtures thereof. The preferred polyhydric alcohol is polyethylene glycol with a molecular weight of 400 or less. The polyethylene glycols suitable for use are well known and commercially available. Polyethylene glycols, which are designated by a number that represents the average molecular weight, range from clear viscous liquids at room temperature, PEGs 200, 300, 400 and 600, to soft solids PEGs, 1000 and 1450, to waxy solids available in the form of flakes or powders, PEGs 3350, 8000 and 14000.

The saturated dialdehyde is selected from the group consisting of malonaldehyde, succinaldehyde, oxaldehyde (glyoxal), adipaldehyde and preferably, glutaraldehyde.

The cationic surface active agent is selected from the group consisting of methylbenzethonium, dodecylamine, hexadecylamine, hexadecylamine hydrochloride, dodecyl aniline, oleyl methylamine ethylene diethylamine methyl sulfate, oleyl benzylamino ethylene diethyamine hydrochloride, sulfate of lauryl pyridinium, octadecyl methylene pyridinium acetate, methyl sulfate of dimethyloctadecyl sulfonium, betaine compound of diethyl aminoacetic acid, octadecyl chloromethyl ether, cetylpyridinium bromide, dodecyltrimethylammonium bromide, hexadecyltrimethylammonium bromide, tetradecyltrimethylammonium bromide, benzalkonium chloride, benzethonium chloride, benzyldimethyldodecylammonium bromide, benzyldimethylhexadecylammonium chloride, benzyldimethyltetradecylammonium chloride, benzyltrimethylammonium methoxide, cetyldimethylethylammonium bromide, decamethonium bromide, dimethyldioctadecylammonium bromide, methylbenzethonium chloride, methyl mixed trialkylammonium chloride, methyltrioctylammonium chloride, 4-picoline dodecyl sulfate, n,n,n'poloxyethylene (10)-n-tallow-1,3-diamino propane and preferably cetylpyridinium chloride.

As used herein, target organisms refers to pathogenic organisms including Staphylococcus areus, Pseudomonas aeruginosa and Salmonella coleraesuis and viruses including HIV, tuberculosis, polio and herpes simples 2 as well as the fungus Trichophyton mentagrophytus, mold, mildew and bacterial spores including Bacillus subtilis, and Colostridium sporogenes.

As used herein, the term non-toxic refers to the acute dermal, acute inhalation and acute oral dosage as defined in 40 Code of Federal Regulations, Section 152.3.

As used herein, the term biodegradable refers to decomposition in the presence of 25 percent organic material within 90 days at 69 degrees F. (Standard Temperature) with moisture content of 100 parts per million.

As used herein, the term challenge refers to a test colony or specimen of $10^6$ specified target pathogenic organisms.

As used herein, the term hypocompatible shall mean no significant or debilitating degradation effects to materials and surfaces exposed to the composition including for example, discoloration, corrosion, cracking, and embrittlement.

The specific monohydric alcohols, polyhydric alcohols, glutaraldehyde and cationic surface active agent and relative ratios complement and interact synergistically to create the desired solubility, specific gravity, conductivity, pH, flash point, boiling point and evaporation required for the effective use of the cold chemical sterilant against the challenge as defined herein on pathogens as described herein with a nontoxic effect as defined herein and with a hypocompatible effect as defined herein on the surfaces described herein.

Further, the polyhydric alcohol reduces the harmful effects of composition if swallowed or sprayed into the eyes or on mucus membranes as well as soothing the skin upon contact. Since the polyhydric alcohol reduces toxicity to human cells the need to dilute the cold sterilant has been eliminated. Tests indicate that the polyhydric alcohol increases the overall effectiveness of the composition against most viruses, mold and mildew and bacterial spores.

Since the cold chemical sterilant was developed for use on a wide variety of instruments and devices the measure of chemical resistance is important to permit broad use and application. To be effective, the cold sterilant must be hypocompatable with CPVC, Epoxy, Polypropylene, PVC, Cyolac (ABS), Phenolic, Nylon, Noryl, Delrin (Acetal), Ryton to 200% F, Kynar, Teflon, Stainless Steel 316, Stainless Steel 304, Carpenter 20, Stainless steel (440), Titanium, Cast Bronze, Cast Iron, Aluminum, Hastelloy C, Carbon/ceramic, Ceramagnet A, Viton, Buna N., Neoprene, Nitrile, Natural rubber, Hypalon, EPDM, Kel-F, Tygon, Silicone, Ceramic and Carbon/graphite.

Comparative results of the cold chemical sterilant with the individual constituents have demonstrated that the combination of interactive ingredients provides a cold chemical sterilant compatible with an expansive range of materials found in a wide variety environments.

In order to accomplish the design criteria of a hypocompatible biodegradable nonaqueous cold chemical sterilant effective against the wide range of pathogenic target organisms described herein, the composition should have a pH of between about 6.0 and 7.5 or essentially neutral, have an effective kill time of about 8 to 12 minutes and leave no toxic residue, a specific gravity of about 0.85, viscosity below 4 and relatively no conductivity.

Standard Association of Official Analitical Chemists (A.O.A.C.) tests of the instant invention have been conducted against the target organisms described herein including Bacillus subtilis, Clostridium sporogenes. The cold sterilant has killed the target organisms within ten minutes.

The effective proportional relationship of the ingredients by weight for the monohydric alcohol is between about 65 percent to 75 percent, for the polyhydric alcohol is between about 4 percent and 16 percent and for both the saturated dialdehyde and cationic surface active agents is between 0.1 to 2.0 percent.

The preferred proportional relationship of the ingredients by weight is about 70 percent for the monohydric alcohol, between about 8 to 12 percent for the polyhydric alcohol, and between about 0.5 to 1.0 percent for both the saturated dialdehyde and cationic surface active agent. As a result there is no dermal toxicity. In addition, since there is no electrolitic activity there is no significant positive interaction between the composition and the instruments.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A hypocompatible nonaqueous cold chemical sterilant for use on medical and dental instrument devices to kill a challenge of target organisms effective against bacteria including Staphylococcus aureus, Pseudomonas aeruginosa, Salmonella chloerasuis and spores, viruses including HIV-I, HIV-II and herples simpex 2, tuberculosis, polio and the fungus Trichophyton mentagrophytus, mold, mildew and spores, said cold chemical sterilant comprising about 65 percent to about 75 percent by weight of a monohydric alcohol selected from the group consisting of isopropyl, methyl, ethyl, n-propyl, n-butyl, tert-butyl and allyl and mixtures thereof, about 4 percent to about 16 percent by weight of a polyhydric alcohol selected from the group consisting of propylene glycol; 1,3 propanediol; 1,2 butanediol, polyethylene glycol; glycerol and 1,4 butanediol and mixtures thereof, less than 2.0 percent by weight of a dialdehyde selected from the group consisting of malonaldehyde, succinaldehyde, oxaldehyde (glyoxal), adipaldehyde and glutaraldehyde and about 0.1 percent to about 2.0 percent by weight of a cationic surface active agent in proportion by weight to denature the proteins to corrupt and penetrate the bacterial spore wall to kill the endospores and other microorganisms wherein the pH of said cold chemical sterilant is between about 6.0 to about 7.5

2. The hypocompatible biodegradable nonaqueous cold chemical sterilant of claim 1 wherein the molecular weight of polyethylene glycol is 400 or less.

3. The hypocompatible nonaqueous cold chemical sterilant of claim 1 wherein said monohydric alcohol is about 70 percent by weight, said polyhydric alcohol is between about 8 to about 12 percent weight, and said dialdehyde and said cationic surface active agent are each less than 1.0 percent by weight.

4. The hypocompatible nonaqueous cold chemical sterilant of claim 1 wherein the pH of said hypocompatible biodegradable nonaqueous cold chemical sterilant is about 7.0.

5. The hypocompatible nonaqueous cold chemical sterilant of claim 1 wherein said dialdehyde is glutaraldehyde less than 1.0 percent by weight and said cationic surface active agent is cetylpyridinium chloride less than 1.0 percent by weight.

6. The hypocompatible nonaqueous cold chemical sterilant of claim 1 wherein said monohydric alcohol is isopropyl alcohol about 70 percent by weight and said polyhydric alcohol is propylene glycol or polyethylene glycol between about 8 and about 12 percent by weight.

* * * * *